(12) United States Patent
Schrader et al.

(10) Patent No.: US 10,328,584 B2
(45) Date of Patent: Jun. 25, 2019

(54) HOLDING ARM FOR POSITIONING A MEDICAL INSTRUMENT OR A MEDICAL APPLIANCE

(71) Applicant: Karl Storz SE & Co. KG, Tuttlingen (DE)

(72) Inventors: Stephan Schrader, Kleinmachnow (DE); Marco Schulze, Berlin (DE); Torsten Siedel, Berlin (DE)

(73) Assignee: Karl Storz SE & Co. KG (DE)

( * ) Notice: Subject to any disclaimer, the term of this patent is extended or adjusted under 35 U.S.C. 154(b) by 443 days.

(21) Appl. No.: 14/676,405

(22) Filed: Apr. 1, 2015

(65) Prior Publication Data
US 2015/0283710 A1 Oct. 8, 2015

(30) Foreign Application Priority Data
Apr. 1, 2014 (DE) .......................... 10 2014 104 557

(51) Int. Cl.
| | | |
|---|---|---|
| *B25J 9/00* | (2006.01) | |
| *B25J 18/00* | (2006.01) | |
| *B25J 17/02* | (2006.01) | |
| *B25J 19/00* | (2006.01) | |
| *A61B 34/30* | (2016.01) | |
| *A61B 17/00* | (2006.01) | |

(52) U.S. Cl.
CPC ............... *B25J 18/00* (2013.01); *A61B 34/30* (2016.02); *B25J 9/0009* (2013.01); *B25J 17/025* (2013.01); *B25J 19/007* (2013.01); *A61B 2017/00526* (2013.01); *Y10T 74/20305* (2015.01)

(58) Field of Classification Search
CPC ........ B25J 18/00; B25J 9/0009; B25J 17/025; B25J 19/007; A61B 34/30; A61B 2017/00526

USPC ..................................... 248/276.1; 74/490.01
See application file for complete search history.

(56) References Cited

U.S. PATENT DOCUMENTS

| | | | | |
|---|---|---|---|---|
| 4,411,402 A * | 10/1983 | Keller | .................. | G01B 5/0002 248/284.1 |
| 5,052,375 A * | 10/1991 | Stark | .................. | A63B 21/4025 482/8 |
| 5,214,749 A * | 5/1993 | Brown | .................. | B25J 9/1643 700/260 |
| 6,446,924 B1 * | 9/2002 | Olson | .................. | F16C 11/103 248/280.11 |
| 7,862,524 B2 * | 1/2011 | Carignan | ............. | A61H 1/0281 601/33 |
| 8,167,872 B2 * | 5/2012 | Schena | .................. | A61B 34/70 606/1 |

(Continued)

FOREIGN PATENT DOCUMENTS

| | | |
|---|---|---|
| DE | 2747048 A1 | 4/1978 |
| DE | 102011119813 A1 | 6/2013 |
| WO | 2014044719 A1 | 3/2014 |

OTHER PUBLICATIONS

European Search Report Application No. EP15162185.1 Completed: Sep. 23, 2015 6 pages.

*Primary Examiner* — Anita M King
(74) *Attorney, Agent, or Firm* — Whitmyer IP Group LLC

(57) ABSTRACT

A segment of a holding arm for positioning a medical instrument or a medical appliance including several node structures, and a strut that rigidly connects two of the several node structures to each other. The strut includes flat structures that are joined to one another.

9 Claims, 15 Drawing Sheets

(56) References Cited

U.S. PATENT DOCUMENTS

2007/0173977 A1 7/2007 Schena
2010/0224023 A1 9/2010 Long et al.
2013/0213170 A1* 8/2013 Kim .................. B25J 18/06
　　　　　　　　　　　　　　　　　　　　74/490.01

* cited by examiner

HOLDING ARM FOR POSITIONING A MEDICAL INSTRUMENT OR A MEDICAL APPLIANCE

FIELD OF THE INVENTION

The present invention is directed to a holding arm for positioning a medical instrument or a medical appliance, to a segment of such a holding arm, and to a method for producing such a segment.

BACKGROUND OF THE INVENTION

An endoscope or another medical instrument that must not be moved, at least at times, during a medical intervention can be held by a holding arm with lockable hinges and degrees of freedom. If the holding arm has a motor drive, the medical instrument can be moved by motor during the medical intervention. Lamps, light sources, monitors and other medical appliances whose position and orientation should be able to be modified, at least from time to time, can also be held by holding arms. Holding arms for these uses generally have several hinges that each facilitate a pivoting movement about one or more axes.

A medical holding arm should at the same time be as stiff as possible such that, with the hinges locked or the drives stopped, a medical instrument or a medical appliance can be held as still as possible even under the effect of an external force. Moreover, a medical holding arm should have a low mass in order to facilitate a movement with low forces and with low power. Moreover, the holding arm should be mechanically robust and easy to maintain, and it should be able to be produced cost-effectively, be easy to assemble and be able to be easily and completely cleaned.

An arm with several segments or portions each connected by hinges has been developed by Festo AG & Co. KG (www.festo.com/cms/de_corp/9770.htm). The ratio between mass and stiffness of the arm is still not optimal, however.

SUMMARY OF THE INVENTION

An object of the present invention is to make available an improved segment for a holding arm, an improved holding arm for positioning a medical instrument or a medical appliance, and an improved method for producing a segment for a holding arm.

This object is achieved by the subjects of the independent claims.

Developments are set forth in the dependent claims.

A segment for a holding arm for positioning a medical instrument or a medical appliance comprises several node structures and a strut that rigidly connects two of the several node structures to each other, wherein the strut comprises flat structures, wherein the flat structures are joined to one another.

At least some of the node structures are provided and designed in particular for the articulated mechanical connection of the segment to a further segment or to another part of a holding arm. For this purpose, a node structure is designed in particular as part of a radial and axial bearing. In particular, a node structure comprises a bearing shell for a plain bearing or roller bearing. The node structures are produced in particular by milling and/or other machining techniques or in a 3D printing method or in a sintering method.

Moreover, each node structure can be provided and designed to be connected directly or indirectly (for example via a shaft connecting two node structures) to a hydraulic, pneumatic, electromotive or other actuator for moving the segment relative to another, adjoining segment or to another part of the holding arm.

The strut is in particular subjected only to tensile and compressive loads and, as an entire structure, does not have to take up any other forces or appreciable forces and moments. However, on account of the spatial configuration of the strut, a bending moment in particular arises in the strut under tensile or compressive loading.

The strut comprises in particular two or three flat structures. The flat structures of the strut are each cut out or bent from sheet metal or other plate-shaped semi-finished product. If the strut comprises two flat structures, these are in particular joined to each other such that an at least approximately T-shaped cross section is obtained. If the strut comprises three flat structures, these are in particular joined to one another such that an approximately I-shaped cross section is obtained. Alternatively, the strut can comprise four flat structures, which are joined to one another such that an approximately trapezoidal cross section is obtained.

The flat structures are in particular integrally bonded to one another by welding, soldering, adhesive bonding or in another way. Alternatively or in addition, the flat structures can be joined with a form fit and/or friction locked by means of one or more bolts, screws, rivets or latching connections.

The production of a segment for a holding arm with struts which are composed of several flat structures can facilitate a cost-effective production with, at the same time, a high degree of mechanical strength. The construction of a segment with several node structures and several struts can allow good access to all the components in the interior of the segment. The segment can in particular be lined with a structure in the form of a lateral surface of a cylinder or of a cone.

In a segment as described here, one of the flat structures has in particular the shape of a cutout of a cylinder lateral surface or of a cone lateral surface.

The flat structure has in particular the shape of a substantially helically strip-shaped cutout of an lateral surface of a circular cylinder or of an elliptical cylinder or of another cylinder. Alternatively, the flat structure has, for example, the shape of a cutout of a cone lateral surface, in particular of a conical spiral or conical helix or, generally, of a loxodrome. If the segment comprises several struts, one of the flat structures of each strut has in particular the shape of a substantially helically strip-shaped cutout of a lateral surface of a cylinder or the shape of a loxodrome on a cone. In this case, these flat structures of two struts are in particular helical in opposite directions or have the shape of two contradirectional loxodromes.

In a segment as described here, the axis of symmetry of the cylinder lateral surface or of the cone lateral surface is in particular parallel to the longitudinal axis of the segment.

If the segment is to be connected, for example via spherical hinges, to adjacent segments or other parts of a holding arm, the longitudinal axis of the segment is the straight line through the center points of the spherical hinges. If the segment is pivotable in each case about a pivot axis relative to adjacent segments or other parts of the holding arm, the longitudinal axis of the segment is in particular the straight line through the center points of shafts in the pivot hinges at the ends of the segment.

Alternatively, one of the flat structures can have the shape of a cutout of a cone lateral surface, in particular of a circular cone lateral surface. In this case, the axis of symmetry of the cone lateral surface or the straight line through tip and center point of the base area is in particular parallel to the longitudinal axis of the segment.

In a segment as described here, one of the flat structures in particular has a tenon, which engages in a corresponding recess in another of the flat structures.

In particular, one or more tenons are provided on one or both of the lengthwise sides of a flat structure that forms a web-like connection between two further flat structures. The one or more tenons are in particular in each case rectangular parallelepipeds or substantially rectangular parallelepipeds. A tenon on a flat structure that engages in a recess on another flat structure can form a friction lock connection between the flat structures, which connection can be strengthened by integral bonding, for example. Moreover, a tenon on a flat structure that engages in a recess on another flat structure can facilitate a transmission of shearing forces between both flat structures.

Alternatively or in addition, one of the flat structures can be provided with snap-fit hooks, resilient structures or other features that facilitate a latching connection. To secure the connection of two flat structures, it is also possible to provide holes, recesses or cavities for the insertion of cotter pins.

In a segment as described here, at least two of the flat structures are in particular joined to each other with a form fit.

As an alternative or in addition to the stated snap-fit hook or another latching connection, it is possible, for example, to provide a screw connection, a rivet connection, or a connection by means of a locking bar. A locking bar can in particular connect two flat structures by means of a projection, lug or bracket on one of the two flat structures being guided through a corresponding slit in the other flat structure and the locking bar being fitted through an opening in the projection, lug or bracket in order to provide a form fit that prevents a withdrawal of the projection, lug or bracket from the slit.

In a segment as described here, the flat structures each have in particular a narrow and elongate shape, wherein the flat structures comprise an inner structure, an outer structure and a connecting web, and wherein a first lengthwise edge of the connecting web is joined to the inner structure, and a second lengthwise edge of the connecting web is joined to the outer structure.

A flat structure has a narrow and elongate shape if its length measured in a first direction (longitudinal direction) is at least twice, in particular at least three times, at least five times or at least eight times its width measured in a second direction perpendicular to the first direction. The edges of the connecting web are in particular joined to the inner structure and/or outer structure at a center line or near a center line of the inner structure and/or outer structure.

In a segment as described here, the inner structure, the connecting web and the outer structure together form in particular an I-shaped cross section of the strut, or the inner structure, two connecting webs and the outer structure together form a trapezoidal or other quadrilateral cross section of the strut.

In the case of a quadrilateral cross section, the flat structures are in particular connected to one another at their edges. A quadrilateral cross section of the strut can provide particular mechanical robustness, especially a particular degree of stiffness of the strut.

In a segment as described here, the first lengthwise edge is in particular substantially straight, and the second lengthwise edge is substantially helical.

In a segment as described here, at least two of the three flat structures are in particular each joined directly to the node structures.

The flat structures are joined integrally to the node structures in particular by welding, soldering, adhesive bonding or in some other way. The node structures can have grooves or slits for receiving the ends of the flat structures, wherein the ends of the flat structures can be held in the grooves by integral bonding and/or with a force fit or friction fit or form fit (in particular by means of a latching connection).

In a segment as described here, an end of a first flat structure in particular bears flat on a first side of a node structure, and an end of a second flat structure bears flat on a second side of the node structure facing away from the first side.

In particular, in relation to the segment, an inner structure bears on an inner side of the node structure and an outer structure bears on an outer side. Flat structures bearing flat on a node structure can facilitate better transmission of forces and moments between the flat structures and the node structure.

In a segment as described here, the ends of the flat structures bearing on opposite sides of the node structure are in particular joined to the node structure.

In particular, the ends of the flat structures are joined integrally to the node structure by adhesive bonding, welding, soldering or in some other way.

In a segment as described here, the node structures are in particular each substantially ring-shaped and, on their outer circumference, have grooves for receiving ends of the flat structures.

The node structures are in particular annular. The node structures can at the same time be designed as bearing shells for plain bearings or roller bearings. The node structures are in particular provided and designed to receive shafts that each form an articulated connection between two adjoining segments.

A segment as described here comprises, in particular, four node structures and four struts, wherein each of the four struts connects two of the four node structures to each other in a mechanically rigid manner.

Each of the four node structures can be mechanically rigidly connected to two struts, which in particular are designed at least partially helically in opposite directions. Each of the four node structures and each of the four struts have in particular the features and properties described here. The four node structures are in particular arranged as the corners of an irregular tetrahedron, wherein the four struts are of equal length. Two node structures not connected directly to each other by a strut are provided and designed to receive a shaft or to form a hinge with an adjacent segment or with another part of a holding arm.

A segment as described here comprises, in particular, six node structures and eight struts, wherein each of the eight struts mechanically rigidly connects two of the six node structures to each other, wherein four of the six node structures are each mechanically rigidly connected to two struts, and wherein two of the six node structures are each mechanically rigidly connected to four struts.

A holding arm for positioning a medical instrument or a medical appliance comprises a segment as described here.

In a method for producing a segment for a holding arm for positioning a medical instrument or a medical appliance, several flat structures are cut out from plate-shaped semi-finished product, bent and/or curved, and joined to form a strut, wherein a first end of the strut is joined to a first node structure and a second end of the strut is joined to a second node structure, and wherein the node structures are joined to further struts.

The flat structures are cut out from aluminum, steel (in particular stainless steel) or other sheet metal, from plastic panels or other plate-shaped semi-finished product, in particular by laser cutting, cutting by water jets, milling, sawing, punching or etching. The flat structures can be elastically and/or plastically deformed by bending and/or curving. The bending and/or curving of the flat structures can take place manually and/or by machine. In particular, the Gaussian curvature of the flat structure designated here as outer structure is 0; a deformation of this kind is designated in particular as bending. The Gaussian curvatures of the structures designated here as inner structure and connecting web are in particular each negative (saddle shape); a deformation of this kind is designated in particular as curving. The bending and the joining of the flat structures to form a strut can be carried out in succession or simultaneously.

In a method as described here, the flat structures each have a narrow and elongate shape and comprise an inner structure, an outer structure and a connecting web, wherein the joining of the flat structures comprises joining a first lengthwise edge of the connecting web to the inner structure and joining a second lengthwise edge of the connecting web to the outer structure.

BRIEF DESCRIPTION OF THE DRAWINGS

Embodiments are explained in more detail below with reference to the attached figures, in which.

DETAILED DESCRIPTION OF THE INVENTION

Figure 1:
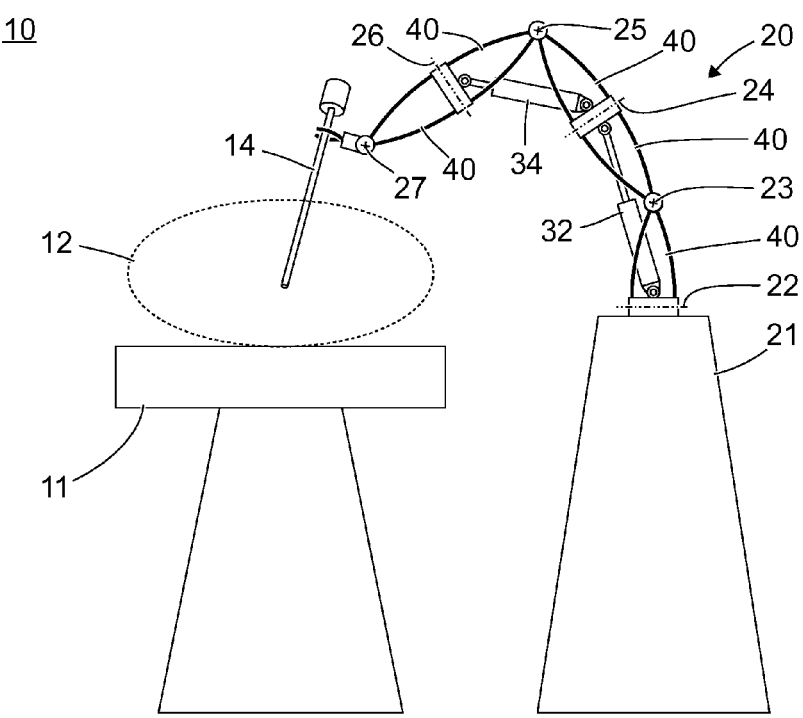
FIG. 1 shows a schematic view of a holding arm for a medical instrument.

FIG. 1 shows a schematic view of an operating theater 10 with an operating table 11 on which is placed a patient 12, indicated by a broken contour line. An endoscope 14 is inserted into the patient 12 and is held in a predetermined position by a holding arm 20. The holding arm 20 sits on a stand 21. Alternatively and in contrast to the view in FIG. 1, the holding arm 20 can be secured on the operating table 11.

The holding arm 20 has several hinges, which each facilitate an angling or a pivoting of two mutually adjoining segments 40 relative to each other about a pivot axis 22, 23, 24, 25, 26, 27. In the simplified view in FIG. 1, the pivot axes 22, 23, 24, 25, 26, 27 are, in alternation, parallel and orthogonal to the plane of the drawing of FIG. 1. The first pivot axis 22, the third pivot axis 24 and the fifth pivot axis 26 are parallel to the plane of the drawing of FIG. 1, while the second pivot axis 23, the fourth pivot axis 25 and the sixth pivot axis 27 are orthogonal to the plane of the drawing of FIG. 1. This easily depicted configuration represents a specific case. When the holding arm 20 is pivoted even by a small angle about the first pivot axis 22, then the third pivot axis 24 and the fifth pivot axis 26 are no longer parallel and the second pivot axis 23, the fourth pivot axis 25 and the sixth pivot axis 27 are no longer orthogonal to the plane of the drawing of FIG. 1. The configuration shown in FIG. 1 was chosen solely for its ease of illustration.

On each pivot axis 22, 23, 24, 25, 26, 27, a drive is provided for pivoting the respective two adjoining segments 40 relative to each other about the pivot axis 22, 23, 24, 25, 26, 27 and/or a means is provided for locking the hinge assigned to the respective pivot axis 22, 23, 24, 25, 26, 27. By way of example, in FIG. 1, two drives 32, 34 (for example hydraulic or pneumatic cylinders or electromotive threaded spindles) are provided for the second hinge 23 and the fourth hinge 25. Drives for the other pivot axes 22, 24, 26, 27 are not shown, so as not to overcomplicate the figure.

Figure 2:
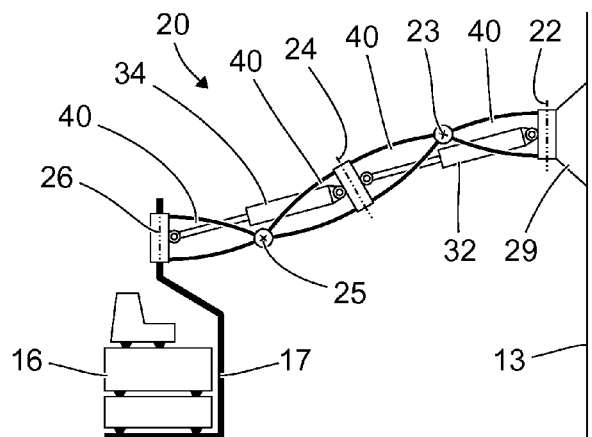
FIG. 2 shows a schematic view of a holding arm for a medical appliance.

FIG. 2 shows a schematic view of a holding arm 20 for holding one or more medical appliances 16, which are arranged on a support 17. In some features and properties, the holding arm 20 shown in FIG. 2 is similar to the holding arm shown in FIG. 1. The nature of the view, in particular the arbitrary configuration of the holding arm 20 in which all the pivot axes 22, 23, 24, 25, 26, 27 are either parallel or orthogonal to the plane of the drawing, is similar to the view in FIG. 1. The holding arm 20 shown in FIG. 2 differs from the holding arm shown in FIG. 1 in particular in that it is secured to a wall 13 of the operating theater 10 by means of a wall mount 29.

Figure 3:
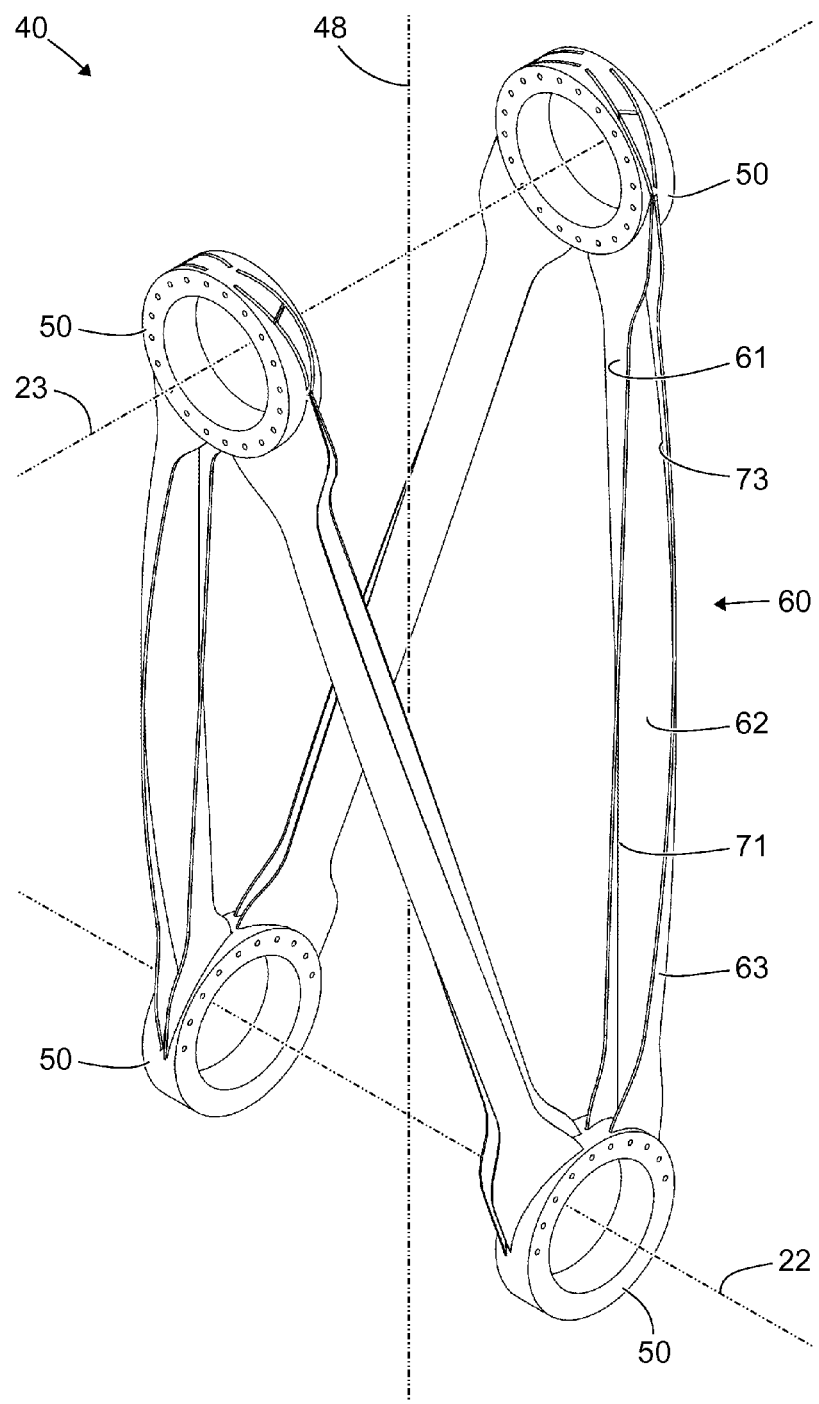
FIG. 3 shows a schematic axonometric view of a segment for a holding arm.

FIG. 3 shows a schematic axonometric view of a segment 40 for forming a holding arm as shown in FIGS. 1 and 2. The segment 40 comprises four annular or substantially annular node structures 50. Two node structures 50 are each arranged rotationally symmetrically with respect to a first pivot axis 22, and two further node structures 50 are arranged symmetrically with respect to a second pivot axis 23. The node structures 50 are in particular designed and arranged to receive two shafts not shown in FIG. 3, one shaft parallel to the first pivot axis 22 and a further shaft parallel to the second pivot axis 23. By way of these shafts, the segment 40 can be connected to adjoining segments or other parts of a holding arm. The node structures 50 are in particular designed as bearings or as parts of bearings, for example as bearing shells for plain bearings or roller bearings, or are provided for receiving bearing shells.

The longitudinal axis 48 of the segment 40 is defined by the center points between the mutually opposite node structures 50. In other words, the longitudinal axis 48 of the segment 40 is the straight line that intersects the pivot axes 22, 23 in each case at the center between the respective node structures.

The pivot axes 22, 23 are each in particular orthogonal to the longitudinal axis 48 of the segment 40. The pivot axes 22, 23 are in particular orthogonal to each other.

The node structures 50 are connected by four struts 60 of equal length. Each strut 60 forms a mechanically rigid connection between a node structure 50 on the first pivot axis 22 and a node structure 50 on the second pivot axis 23. Each node structure 50 on the first pivot axis 22 is connected by a respective strut 60 to both node structures 50 on the second pivot axis 23 in a mechanically rigid manner. Each node structure 50 on the second pivot axis 23 is connected by a respective strut 60 to each node structure 50 on the first pivot axis 22 in a mechanically rigid manner.

Each strut 60 is straight or, as shown in FIG. 3, at least partially helical. The segment 40 is in particular designed such that each strut 60 has to take up substantially only tensile forces or pressure forces. Each strut 60 is composed of three plate-shaped structures 61, 62, 63. The plate-shaped structures 61, 62, 63 are each curved or twisted.

Each strut 60 comprises a twisted plate-shaped inner structure 61, a twisted plate-shaped connecting web 62 and a bent plate-shaped outer structure 63. The fact that the inner structure 61 and the connecting web 62 are twisted means that, starting from an original flat state, they are each extended at their lengthwise edges and/or compressed in the central areas between the lengthwise edges. The plate-shaped inner structure 61, the plate-shaped connecting web 62 and the plate-shaped outer structure 63 can each be plastically and/or elastically deformed (twisted or bent). The inner structure 61, the connecting web 62 and the outer structure 63 are arranged such that the cross section of the strut 60 is substantially I-shaped. In particular, a first lengthwise edge 71 of the connecting web 62 is joined to the inner structure 61 and a second lengthwise edge 73 of the connecting web 62 is joined to the outer structure 63.

Figure 4:
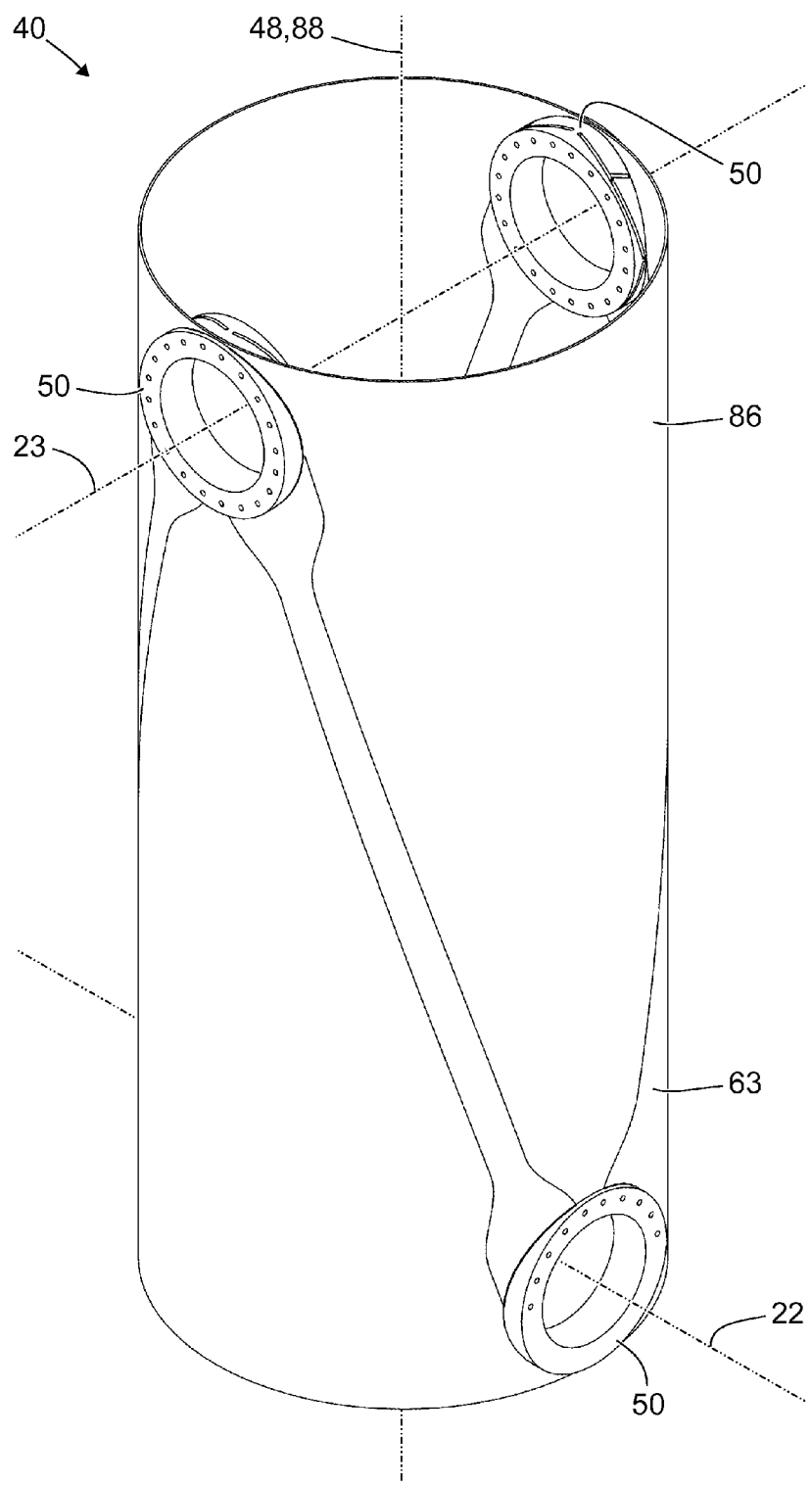
FIG. 4 shows a further schematic axonometric view of parts of the segment from FIG. 3.

FIG. 4 shows a further schematic axonometric view of parts of the segment 40 from FIG. 3. In FIG. 4, only the node structures 50 and the outer structures 63 are shown, not the inner structures 61 and the connecting webs 62. Moreover, FIG. 4 shows a circular cylinder lateral surface 86. The cylinder axis 88 of the circular cylinder lateral surface 86, i.e. the straight line to which the circular cylinder lateral surface 86 is both cylindrically symmetrical (translation invariant) and also rotationally symmetrical, coincides with the longitudinal axis 48 of the segment 40 or is identical thereto.

The outer structures 63 are substantially helically strip-shaped cutouts of the circular cylindrical lateral surface 86 that are widened at the ends joined to the node structures 50. The outer structures 63 of two struts 60, which are connected to the same node structure 50, each lie on two contradirectional helices.

Figure 5:
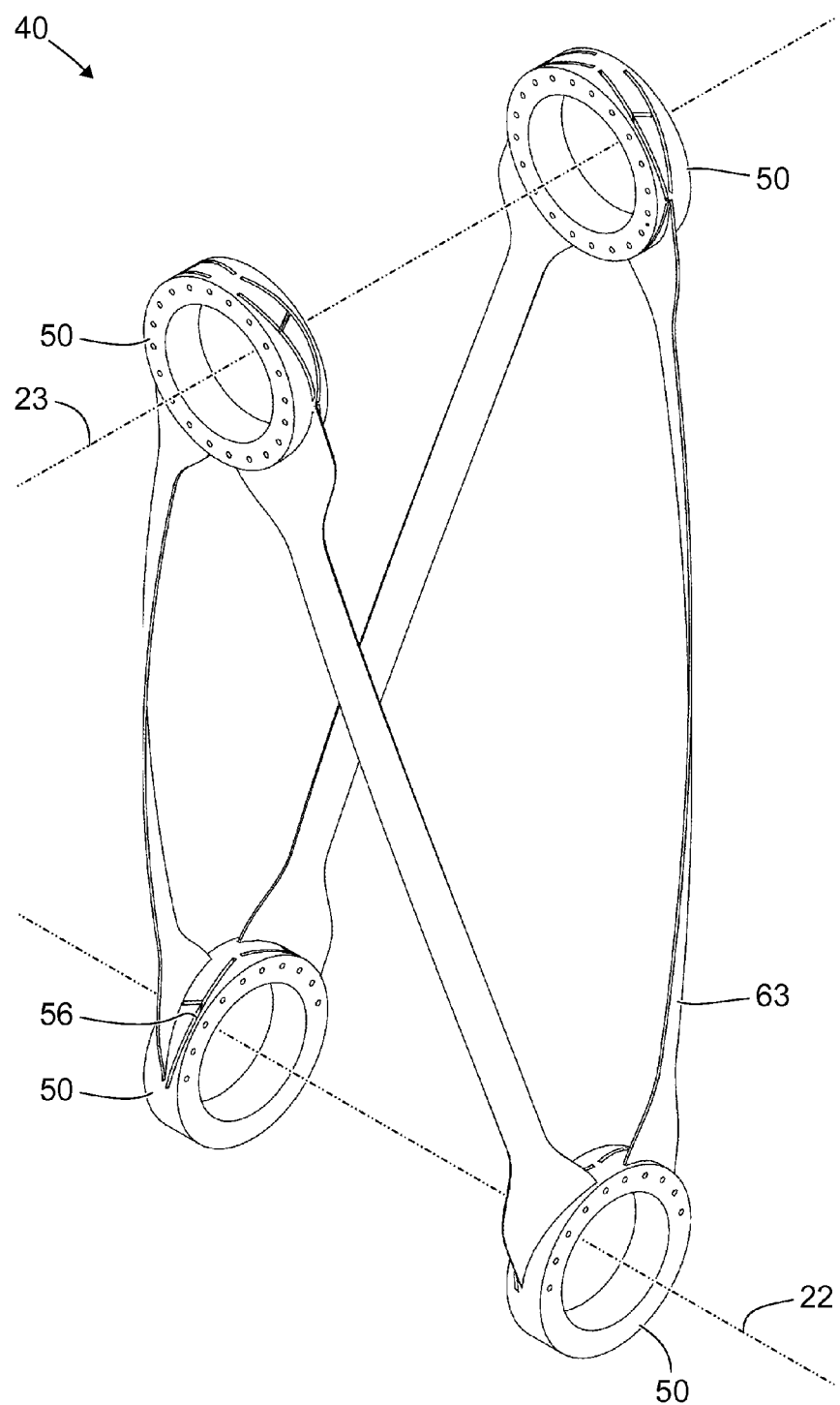
FIG. 5 shows a further schematic axonometric view of parts of the segment from FIGS. 3 and 4.

FIG. 5 shows a further schematic axonometric view of parts of the segment from FIGS. 3 and 4. In FIG. 5, in the same way as in FIG. 4, only the node structures 50 and the outer structures 63 are shown. In contrast to FIG. 4, the circular cylinder lateral surface is not shown in FIG. 5. Grooves 56 that can be seen in the node structures 50 are provided to receive the ends of the inner structures 61 and of the connecting webs 62 (cf. FIG. 3), which are not shown in FIG. 5.

Figure 6:
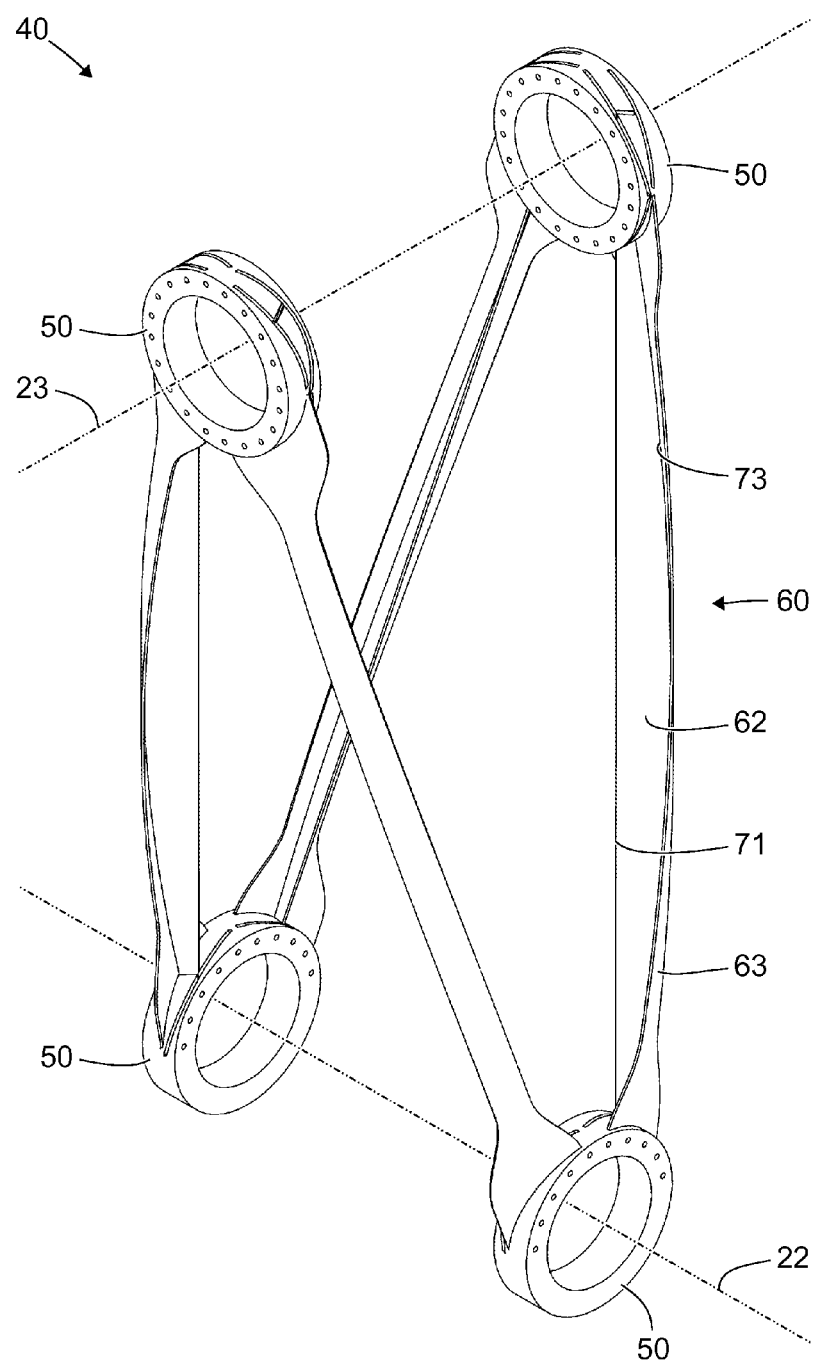
FIG. 6 shows a further schematic axonometric view of parts of the segment from FIGS. 3 to 5.

FIG. 6 shows a further schematic axonometric view of parts of the segment from FIGS. 3 to 5. The view in FIG. 6 differs from that of FIG. 3 in that the inner structures are not shown. The view in FIG. 6 differs from that of FIG. 5 in that, in addition to all the node structures 50 and outer structures 63, the connecting webs 62 of all the struts 60 are also shown. The first edges 71 of the connecting webs 62 are straight or substantially straight.

The configuration shown in FIG. 6 represents an alternative to the configuration shown in FIG. 3. In the configuration shown in FIG. 6, the struts 60 each have a T-shaped cross section.

Figure 7:
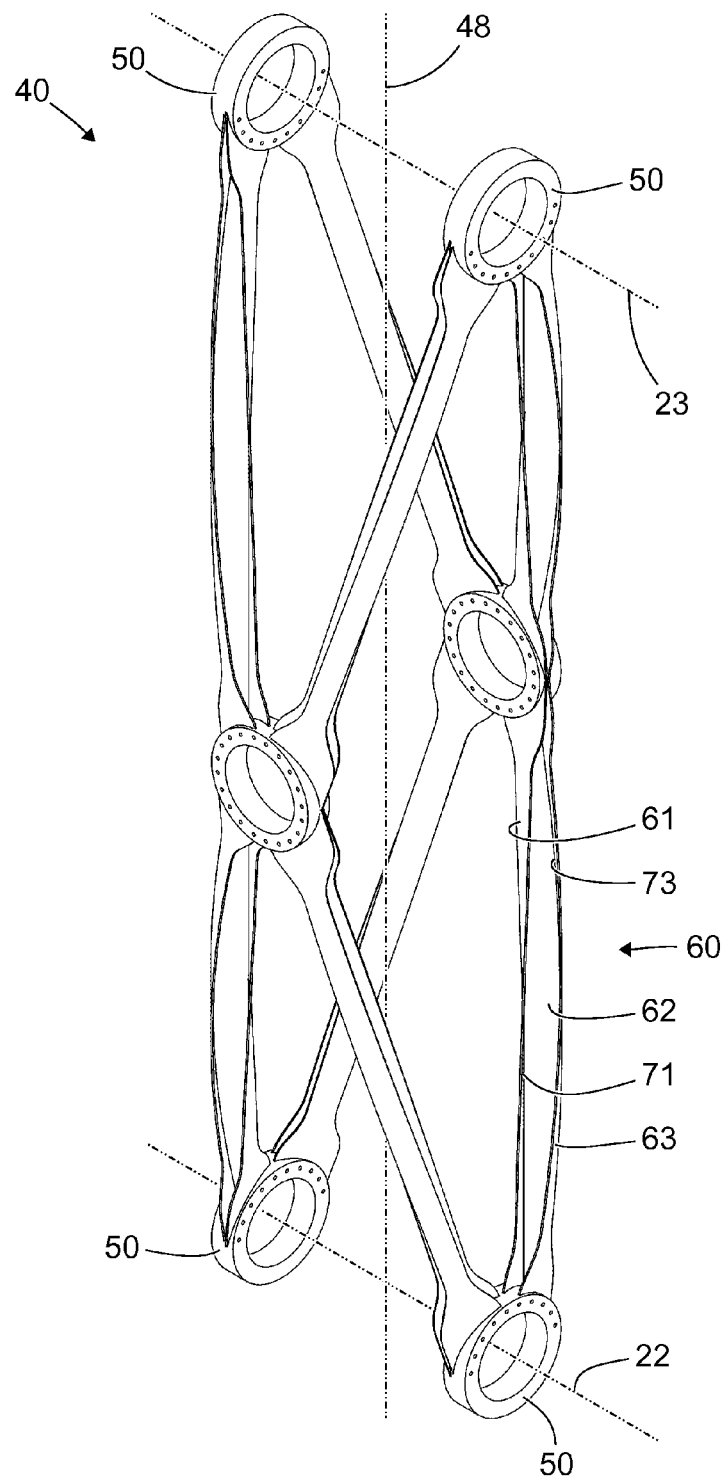
FIG. 7 shows a schematic axonometric view of a further segment for a holding arm.

FIG. 7 shows a schematic axonometric view of a further segment 40 for a holding arm. The segment 40 shown in FIG. 7 differs from the segment shown in FIGS. 3 to 6 in that it comprises six node structures 50 instead of four and comprises eight struts 60 instead of four.

The segment 40 shown in FIG. 7 takes the form of two segments, of the kind shown in FIGS. 3 to 6, which are arranged in mirror symmetry to each other and are mechanically rigidly connected to each other via common node structures 50. Four node structures 50 arranged at the ends of the segment 40 and defining pivot axes 22, 23 are each mechanically rigidly connected by two struts 60 and, by way of these, to one of two central node structures. Each of the central node structures 50 not assigned to one of the two pivot axes 22, 23 is mechanically rigidly connected by four struts to all four node structures assigned to the pivot axes 22, 23.

The segments shown in FIGS. 3 to 7 can be supplemented by a lining, which is not shown in the figures. The lining has in particular the form of an lateral surface of a circular cylinder. This lateral surface of a circular cylinder is similar in particular to the circular cylinder lateral surface shown in FIG. 4, but it has a slightly larger diameter, such that in particular the inner side of the lining bears externally on the struts 60.

With a lining of this kind, components and structures arranged in the interior of the segment can be protected from environmental effects and damage. Particularly in the case of the segment shown in FIG. 7, the lining can further serve to take up forces and to stiffen the segment. Above all, the lining can in each case create a mechanically stiff connection between two end-position node structures lying on the same side of the longitudinal axis 48.

Figure 8:
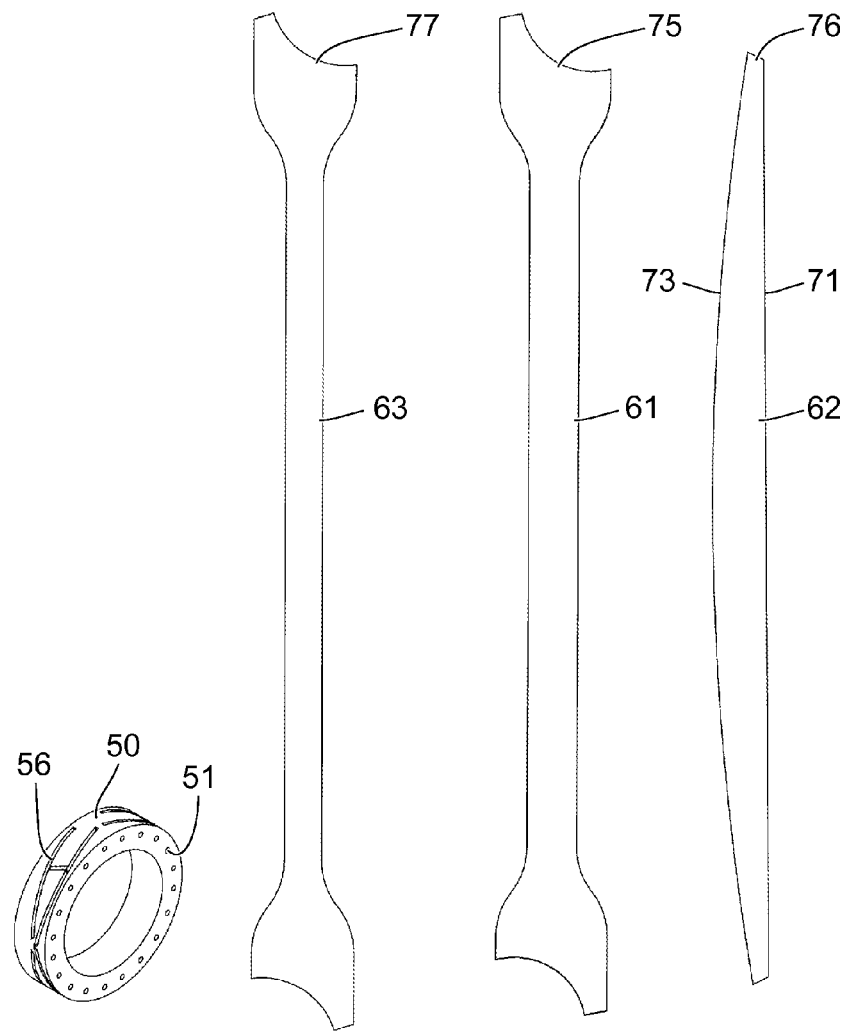
FIG. 8 shows a schematic view of structures for a segment.

FIG. 8 shows a schematic view of structures for one of the segments shown in FIGS. 3 to 7. A node structure 50 is shown in an axonometric view.

The flat structures 61, 62, 63, i.e. the inner structure 61, the connecting web 62 and the outer structure 63, are shown in a simple plan view and in the flat shape prior to the production of a strut. The connecting web 62 has a straight or substantially straight first edge 71, in particular for integrally bonded connection to the inner structure 61, and a curved second edge 73, in particular for integrally bonded connection to the outer structure 63.

The node structure 50 is produced in particular by means of milling and/or another machining technique or by means of a 3D printing method or by means of a sintering method. The node structure 50 has grooves 56 for receiving the ends 75, 76, 77 of the flat structures 61, 62, 63. Optionally, the node structure 50 has bores 51. By way of the bores 51, the ends 75, 76, 77 of the flat structures 61, 62, 63 can be joined in the grooves 56, for example by laser welding. Alternatively, the ends 75, 76, 77 of the flat structures 61, 62, 63 can have corresponding bores and, after being inserted into the grooves 56, can be held with a form fit on the node structure 50 by means of pins inserted into the bores 52.

Figure 9:
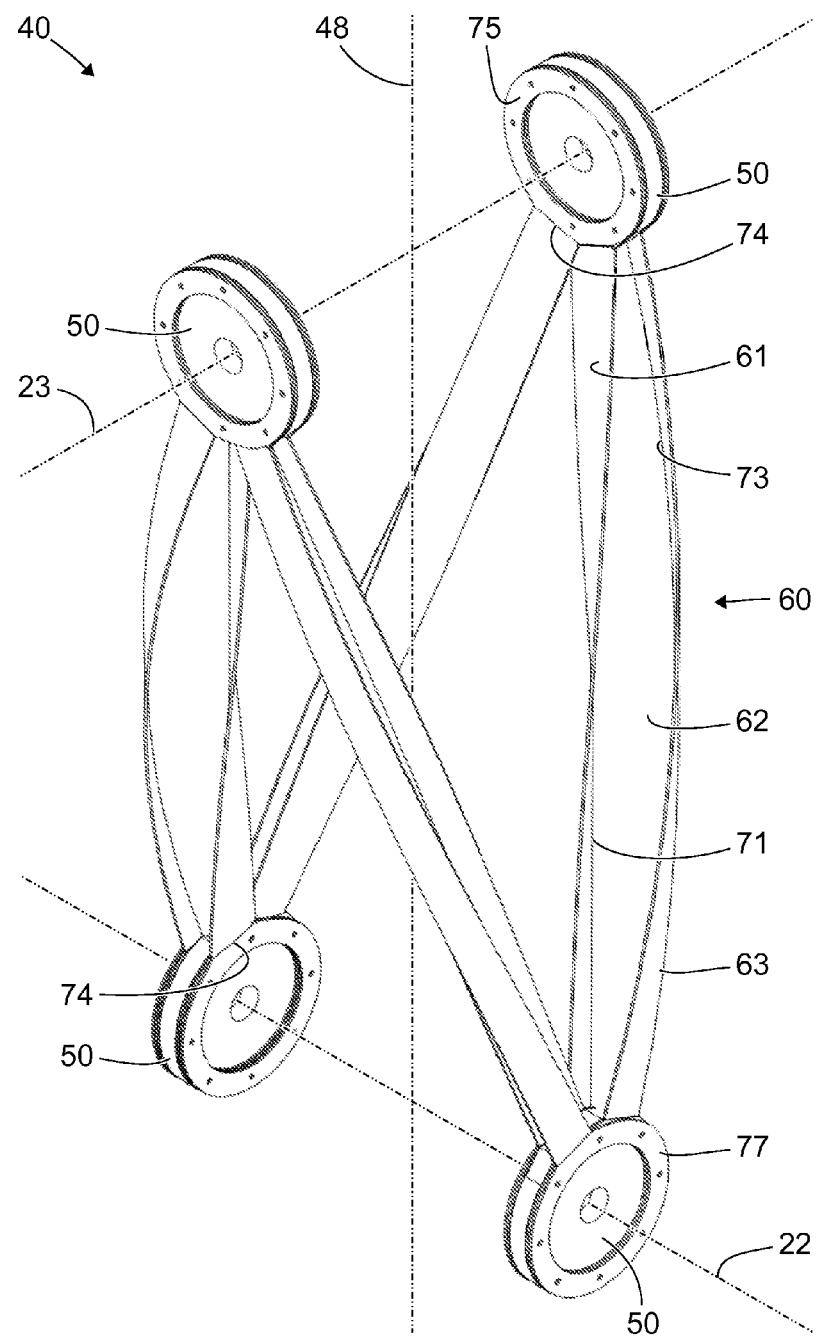
FIG. 9 shows a schematic axonometric view of a further segment for a holding arm.

FIG. 9 shows a schematic axonometric view of a further segment 40 for a holding arm which, in terms of some features, properties and functions, is similar to or corresponds to the segments shown in FIGS. 3 to 8.

The segment 40 shown in FIG. 9 differs from the segments shown in FIGS. 3 to 6 in particular in terms of a different connection between the inner structures 61 and the outer structures 63, on the one hand, and the node structures 50, on the other hand. The inner structures 61 and the outer structures 63 are each ring-shaped at their ends 75, 77. The ends 75 of the inner structures 61 bear flat on the inner sides of the node structures 50 and in particular are integrally bonded thereto. The inner side of a node structure 50 is in each case the surface of the node structure 50 facing toward the opposite node structure. The ends 77 of the outer structures 63 bear on the outer sides of the node structures 50 and in particular are integrally bonded thereto. The outer side of a node structure 50 is in each case the surface of the node structure 50 facing away from the opposite node structure. As an alternative or in addition to an integrally bonded connection, it is also possible for a form-fit connection to be provided, for example by means of screws or rivets.

In the transition area to the ring-shaped ends 75 bearing flat on the node structures 50, the inner structures 61 each have bending edges 74. On the outer structures 63, the transitions to the ring-shaped ends 77 bearing flat on the node structures 50 are smooth.

Figure 10:
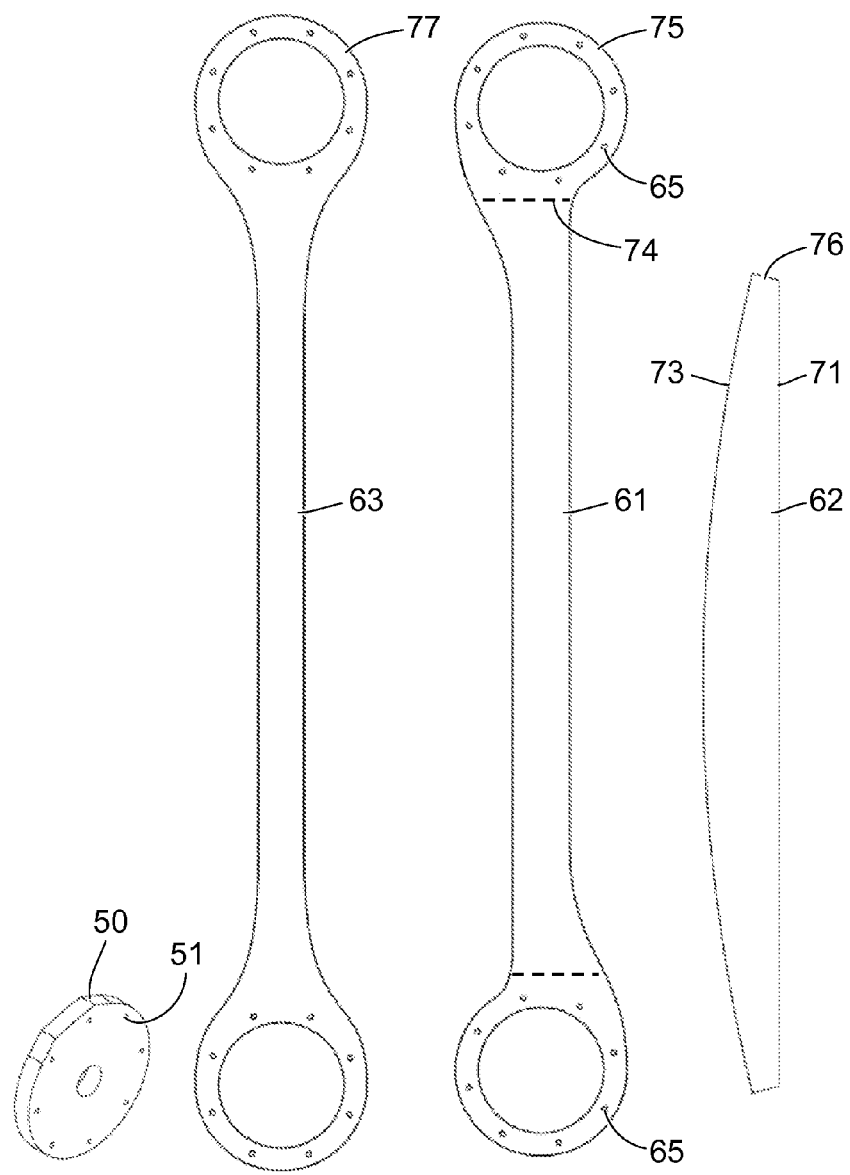
FIG. 10 shows a schematic view of structures for a segment.

FIG. 10 shows a schematic view of structures for the segment shown in FIG. 9. A node structure 50 is shown in an axonometric view.

The flat structures 61, 62, 63, i.e. the inner structure 61, the connecting web 62 and the outer structure 63, are shown in a simple plan view and in the flat shape prior to the production of a strut. The connecting web 62 has a straight or substantially straight first edge 71, in particular for integrally bonded connection to the inner structure 61, and a curved second edge 73, in particular for integrally bonded connection to the outer structure 63.

The node structure 50 has a simple shape with two parallel and flat surface areas and, lying between these, an edge area of constant width. On account of its simple shape, the node structure 50 can be cut out from plate-shaped semi-finished product.

Optionally, the node structure 50 has bores 51. The ends 75, 76, 77 of the flat structures 61, 62, 63 have corresponding bores 65. Rivets can be introduced into the bores 51 in the node structures 50 and into the bores 65 in the ends 75, 76, 77 of the flat structures 61, 62, 63, said rivets connecting the ends 75, 76, 77 of the flat structures 61, 62, 63 to the node structures 50. At each bending edge 74, a perforation or a linear weakening of the plate-shaped material can be provided in order to make canting easier.

Figure 11:
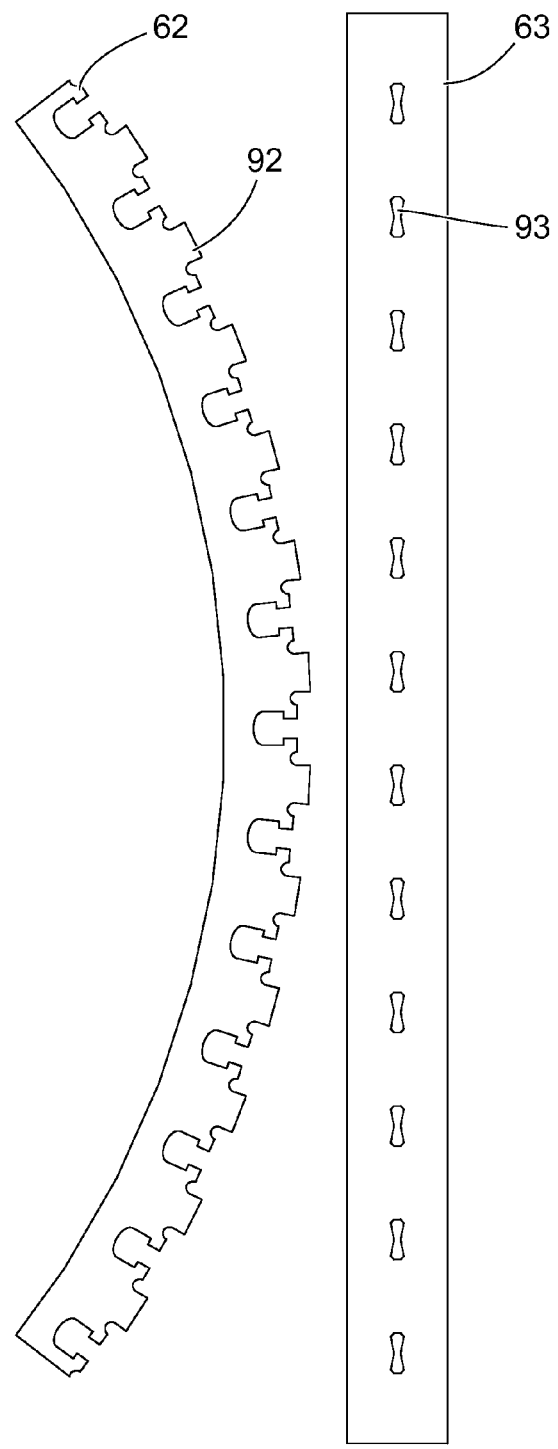
FIG. 11 shows a schematic view of structures for a further segment for a holding arm.

FIG. 11 shows a schematic view of flat structures 62, 63 for an alternative embodiment of a strut. The flat structures 62, 63 are designed to jointly form a T-shaped cross section of a bent, in particular helically bent strut.

A flat structure 62 has rectangular tenons 92, which are provided, arranged and designed to engage in corresponding recesses 93 in the other flat structure 63. In addition to the form fit engagement between the tenons 92 and the recesses 93, the flat structures can be joined by a force fit or friction fit and/or by integral bonding (welding, soldering, adhesion, etc.). As an alternative or in addition, cotter pins or clips, for example, can hold the flat structures 62, 63 together.

In a departure from the view in FIG. 11, a further flat structure can be provided, similarly to the segments shown in FIGS. 3 to 8. Together with this further flat structure, it is possible to produce an I-shaped cross section of a strut. The flat structure 62 can be connected to the further flat structure (not shown in FIG. 11) with a form fit (similarly to the flat structure 61) and/or with an integral bond or a force fit or friction fit.

In a departure from the views in FIGS. 3 to 9, the outer surfaces of a segment (in particular the outer structures 63) do not take the shape of cutouts from a cylinder lateral surface but instead, for example, the shape of cutouts from a cone lateral surface. A slightly conical shape of this kind of the axially symmetrical surface in which the outer structures 63 lie is suggested in FIG. 9 but not shown explicitly. In particular, each flat outer structure 63 has the shape of a conical spiral or a conical helix or generally the shape of a loxodrome.

Figure 12:
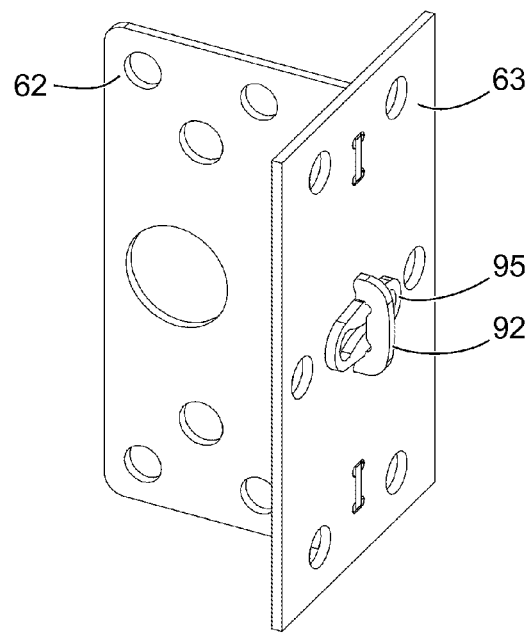
FIG. 12 shows a schematic axonometric view of a connection between two structures.

FIG. 12 shows a schematic axonometric view of a possible form-fit connection of two flat structures 62, 63, in particular of a connecting web 62 and of an outer structure 63. FIG. 12 shows only details of both flat structures 62, 63 in order to illustrate the form-fit connection. Apart from features described below concerning the edges in particular, the entire flat structure 62, 63 can in each case have a shape, in particular a contour, as is shown in FIG. 8, 10 or 11. The flat structures 62, 63 have circular openings, which can be provided to lessen the mass and/or as securing points.

The connecting web 62 has a lug or bracket or tenon 92 with a recess 94. The tenon 92 is inserted through a slit-shaped recess 93 in the outer structure 63. A resilient locking bar 95 is fitted into the recess 94 in the tenon 92. The resilient locking bar 95 bears on the outer side of the outer structure 63 facing away from the connecting web 62 and thus provides a form fit that prevents the tenon 92 on the connecting web 62 from being pulled out from the recess 92 in the outer structure 63.

Figure 13:
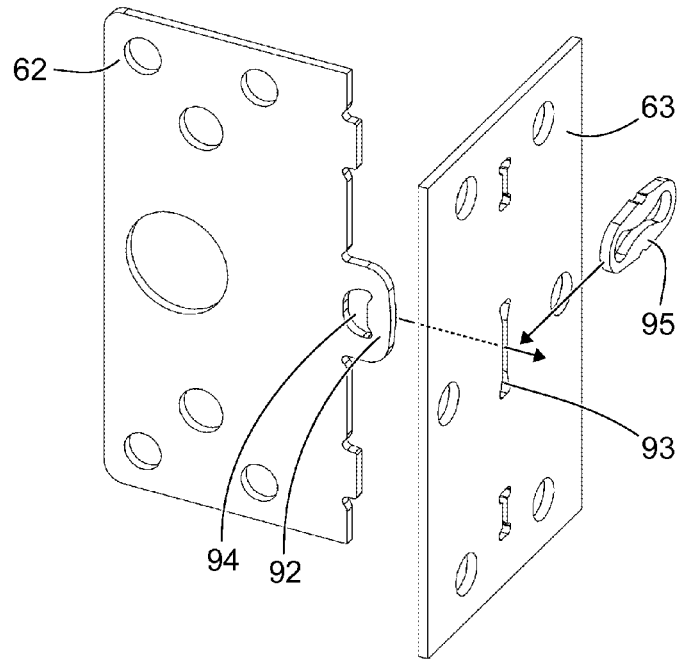
FIG. 13 shows a schematic axonometric view of the structures from FIG. 12 in a separated state.

FIG. 13 shows a further schematic axonometric view of the connecting web 62, the outer structure 63 and the resilient locking bar 95 from FIG. 12. The connecting web 62, the outer structure 63 and the resilient locking bar 95 are shown spaced apart from one another. Arrows indicate how the tenon 92 can first of all be inserted into the slit-shaped recess 93 at the outer structure 63, and then the resilient locking bar 95 can be inserted into the recess 94 in the tenon 92. The resilient locking bar 95 has substantially the shape of a shallow ring. Grooves on the resilient locking bar 95 are provided for the purpose of receiving edges of the recess 94 in the tenon and thereby holding the locking bar 95 with a form fit in the position shown in FIG. 12.

Figure 14:
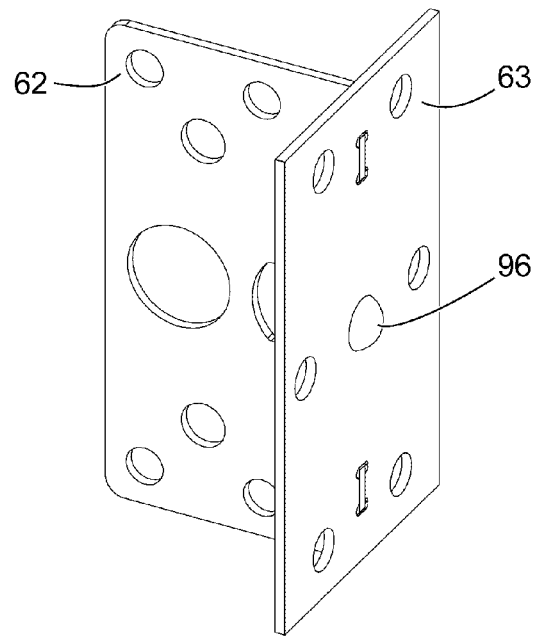
FIG. 14 shows a schematic axonometric view of a connection between two structures.

FIG. 14 shows a schematic axonometric view of a further possible form-fit connection of two flat structures 62, 63, in particular of a connecting web 62 and of an outer structure 63. The connecting web 62 and the outer structure 63 are connected to each other with a form fit by means of a rivet 96.

Figure 15:
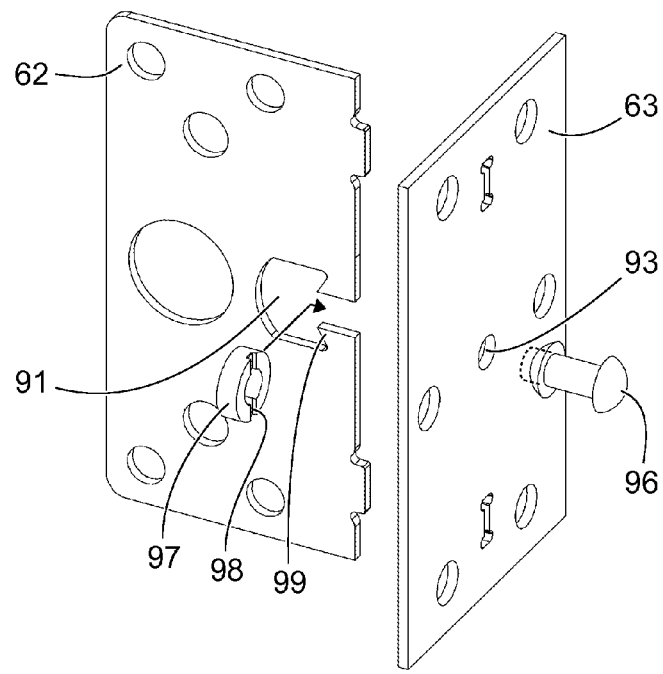
FIG. 15 shows a schematic axonometric view of the structures from FIG. 14 in a separated state.

FIG. 15 shows a further schematic axonometric view of the connecting web 62, the outer structure 63 and the rivet 96 from FIG. 14. The nature of the view corresponds to that of FIG. 13, with the rivet 96 in FIG. 15 being shown by broken lines in its form prior to insertion and deformation, and by solid lines in its form when already deformed.

The connecting web 62 has a bay-shaped recess 91 with two lugs 99. An arrow indicates how a ring 97 with grooves 98 is first of all inserted into the bay-shaped recess 91 on the connecting web 62. Each groove 98 on the ring 97 receives a lug 99 on the bay-shaped recess. The rivet 96 is then inserted into and deforms the recess 93 in the outer structure 63 and the ring 97, so as to connect the ring 97, and therefore also the connecting web 62, to the outer structure 63 with a form fit. In a departure from the view in FIG. 15, the deformation of the rivet can take place at the opposite end thereof.

Figure 16:
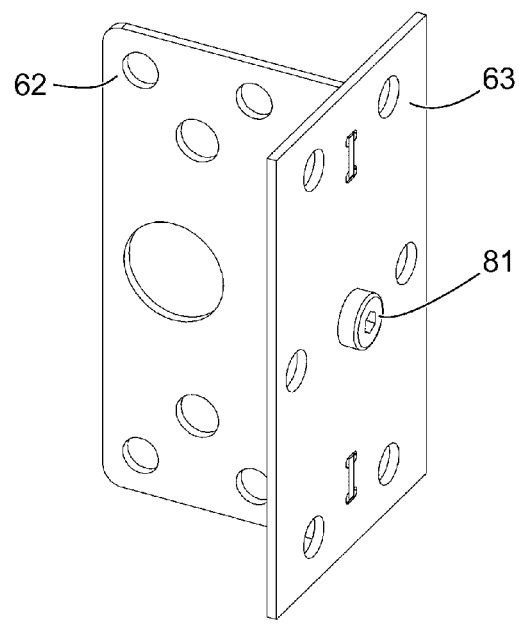
FIG. 16 shows a schematic axonometric view of a connection between two structures.

FIG. 16 shows a schematic axonometric view of a further possible form-fit connection of two flat structures 62, 63, in particular of a connecting web 62 and of an outer structure 63. The connecting web 62 and the outer structure 63 are connected to each other by means of a screw 81 and of a screw nut.

Figure 17:
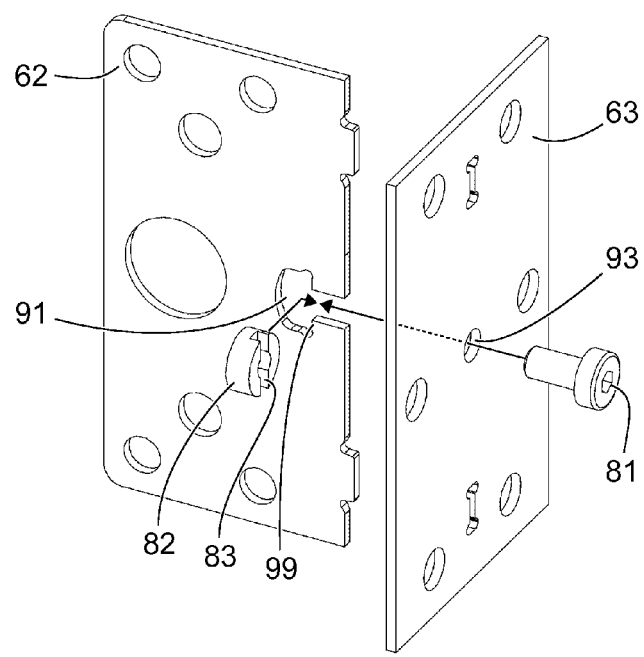
FIG. 17 shows a schematic axonometric view of the structures from FIG. 16 in a separated state.

FIG. 17 shows a further schematic axonometric view of the connecting web 62, the outer structure and the screw 81 from FIG. 14, and also of the screw nut 82 corresponding to the screw 81. The nature of the view corresponds to that of FIGS. 13 and 15.

The connecting web 62 has a bay-shaped recess 91 with two lugs 99. An arrow indicates how a screw nut 82 with grooves 83 is first of all inserted into the bay-shaped recess 91 on the connecting web 62. Each groove 83 on the nut 82 receives a lug 99 on the bay-shaped recess. A further arrow indicates how the screw 81 is then inserted through the recess 93 in the outer structure 63 into the screw nut 82 and screwed into the latter, in order to connect the screw nut 82, and therefore also the connecting web 62, to the outer structure 63 with a form fit.

Figure 18:
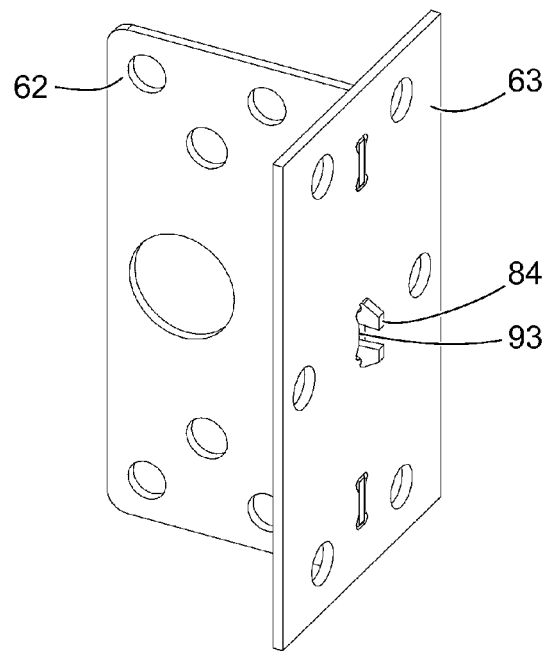
FIG. 18 shows a schematic axonometric view of a connection between two structures.

FIG. 18 shows a schematic axonometric view of a further possible form-fit connection of two flat structures 62, 63, in particular of a connecting web 62 and of an outer structure 63. The connecting web 62 and the outer structure 63 are connected to each other by means of two locking lugs 84.

Figure 19:
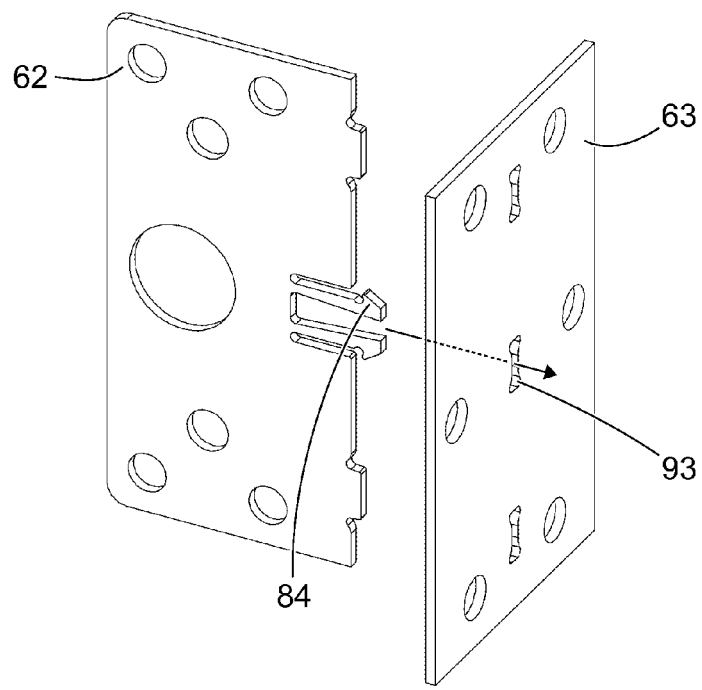
FIG. 19 shows a schematic axonometric view of the structures from FIG. 18 in a separated state.

FIG. 19 shows a further schematic axonometric view of the connecting web 62 and of the outer structure 63 from FIG. 14. The nature of the view corresponds to that of FIGS. 13, 15 and 17.

The connecting web 62 has a bay-shaped recess 91 with two lugs 99. An arrow indicates how the locking hooks 84 are guided through the slit-shaped recess 93 in the outer structure 63. The locking hooks 84 are elastically deformed briefly by the edges of the slit-shaped recess 93 before the locking hooks 84 adopt the positions shown in FIG. 18, in which they connect the connecting web 62 with a form fit to the outer structure 63.

Figure 20:
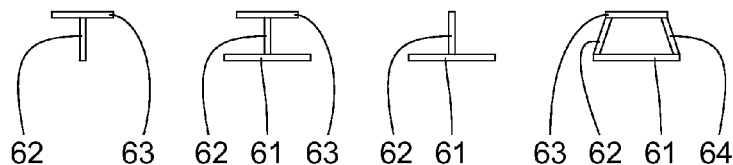
FIG. 20 shows a schematic view of alternative cross sections of a strut.

FIG. 20 shows a schematic view of alternative cross sections of a strut. A T-shaped cross section of a strut with a web 62 and an outer structure 63 is shown on the far left in FIG. 20. This cross section corresponds to the configuration shown in FIG. 6.

Next to this, an I-shaped cross section of a strut composed of an inner structure 61, a connecting web 62 and an outer structure 63 is shown. This cross section corresponds to the configuration shown in FIGS. 3 and 7.

A T-shaped cross section of a strut composed of an inner structure 61 and of a web 62 is shown third from the left.

On the far right, FIG. 20 shows a rectangular, namely trapezoidal, cross section of a strut with an inner structure 61, two connecting webs 62, 64 and an outer structure 63.

Figure 21:
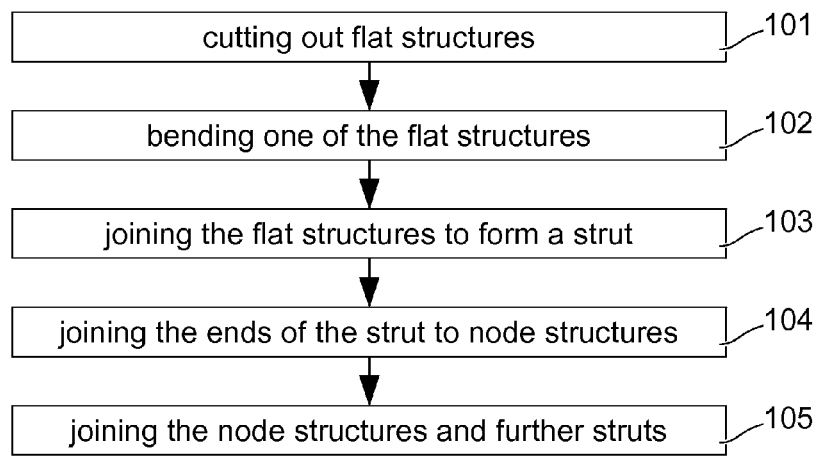
FIG. 21 shows a schematic flow chart of a method for producing a segment for a holding arm.

FIG. 21 shows a schematic flow chart of a method for producing a segment for a holding arm for positioning a medical instrument or a medical appliance. Although the method is also suitable for producing a segment that has features, properties and functions deviating from the views in FIGS. 3 to 9, reference signs from FIGS. 3 to 9 are used below by way of example in order to make matters clearer.

In a first step 101, the flat structures 61, 62, 63, 64 are cut out from one or more different sheets of metal or other plate-shaped semi-finished products, for example by laser cutting, cutting by water jets, milling, sawing, etc.

In a second step 102, at least one of the flat structures 61, 62, 63, 64 is curved or bent. In particular, an inner structure 61 and one or more connecting webs 62, 64 are twisted, such that they each have a negative Gaussian curvature, and an outer structure is bent such that it furthermore has a vanishing Gaussian curvature, in particular the form of a strip-shaped cutout of a circular cylinder lateral surface. The curving and/or bending of the flat structures can be done manually and/or by machine.

In a third step 103, the flat structures 61, 62, 63, 64 are joined to form a strut 60. The flat structures 61, 62, 63, 64 are joined to one another with an integrally bonded connection, a force fit, a friction fit and/or a form fit, in particular by laser welding or other welding, soldering, adhesive bonding or some other way.

In a fourth step 104, the ends of the strut 60 formed by means of the first step 101, second step 102 and third step 103 are each joined to a node structure 50. In a fifth step 105, the node structures 50 are joined to further struts 60 and the latter to further node structures 50.

REFERENCE SIGNS

10 operating theater
11 operating table
12 patient
13 wall of the operating theater 10
14 medical instrument, in particular endoscope
16 medical appliance
17 support for the medical appliance 16
20 holding arm for positioning the medical instrument 14 or the medical appliance 16
21 stand for holding arm 20
22 pivot axis on the holding arm 20
23 pivot axis on the holding arm 20
24 pivot axis on the holding arm 20
25 pivot axis on the holding arm 20
26 pivot axis on the holding arm 20
27 pivot axis on the holding arm 20
29 wall mount for holding arm 20
32 drive for pivot axis 23
34 drive for pivot axis 25
40 segment of the holding arm 20 between two hinges 30
48 longitudinal axis of the segment 40
50 node structure
51 bore for pin or rivet
56 groove in the node structure for receiving an end 75, 76, 77 of a flat structure 61, 62, 63 of the strut 60
60 strut
61 inner structure, or first flat structure of the strut 60
62 connecting web, or second flat structure of the strut 60
63 outer structure, or third flat structure of the strut 60
64 second connecting web, or fourth flat structure of the strut 60
65 bore for rivet
71 first lengthwise edge of the connecting web 62
73 second lengthwise edge of the connecting web 62
74 bending edge on the inner structure 61
75 end of the inner structure 61
76 end of the connecting web 62

77 end of the outer structure 63
81 screw
82 screw nut
83 groove in screw nut
84 locking hook
86 circular cylinder lateral surface
88 cylinder axis of the circular cylinder lateral surface 86
91 bay-shaped recess in the connecting web 62
92 tenon on connecting web 62
93 recess in the outer structure 63
94 recess in the tenon 92
95 resilient locking bar
96 rivet
97 ring
98 groove in ring 97
99 lug on the flat structure 62
101 first step (cutting out flat structures)
102 second step (bending one of the flat structures)
103 third step (joining the flat structures to form a strut)
104 fourth step (joining the ends of the struts to a node structure)
105 fifth step (joining the node structures and further struts)

The invention claimed is:

1. A segment for a holding arm for positioning a medical instrument or a medical appliance, comprising:
   several node structures;
   a strut that rigidly connects two of the several node structures to each other;
   the strut having flat structures that are joined to one another;
   wherein at least two of the flat structures are joined to each other with a form fit; and
   wherein one of the flat structures has a tenon, which engages in a corresponding recess in another of the flat structures.

2. The segment according to claim 1, wherein the several node structures are four node structures and the strut is a first strut, and the segment further comprises a second strut, a third strut, and a fourth strut; and
   each of the four struts connects two of the four node structures to each other in a mechanically rigid manner.

3. The segment according to claim 1, wherein the segment is integrated into a holding arm for positioning the medical instrument or the medical appliance.

4. A segment for a holding arm for positioning a medical instrument or a medical appliance, comprising:
   several node structures;
   a strut that rigidly connects two of the several node structures to each other;
   the strut having flat structures that are joined to one another;
   wherein the flat structures each have a narrow and elongate shape;
   wherein the flat structures comprise an inner structure, an outer structure, and a connecting web;
   wherein a first lengthwise edge of the connecting web is joined to the inner structure, and a second lengthwise edge of the connecting web is joined to the outer structure; and
   wherein the inner structure, the connecting web, and the outer structure together form an I-shaped cross section of the strut, or the inner structure, the connecting web, a second connecting web, and the outer structure together form a quadrilateral cross section of the strut.

5. The segment according to claim 4, wherein the first lengthwise edge is substantially straight and the second lengthwise edge is substantially helical.

6. A segment for a holding arm for positioning a medical instrument or a medical appliance, comprising:
   several node structures;
   a strut that rigidly connects two of the several node structures to each other;
   the strut having flat structures that are joined to one another;
   wherein the node structures are each substantially ring-shaped and have grooves on their outer circumference, each of the grooves are configured to receive an end of one of the flat structures.

7. A segment for a holding arm for positioning a medical instrument or a medical appliance, comprising:
   several node structures;
   several struts each rigidly connecting two of the several node structures to each other;
   at least one of the several struts having a first flat structure extending from a first of the several node structures to a second of the several node structures, and a second flat structure extending from the first of the several node structures to the second of the several node structures; and
   the first flat structure is joined to the second flat structure by a connecting structure extending substantially from a first end of the first and second flat structures to a second end of the first and second flat structures;
   wherein at least one of the first flat structure and the second flat structure has a shape of a cutout of a lateral surface of a cylinder or a cone.

8. The segment according to claim 7, wherein at least one of the first flat structure and the second flat structure has a shape of a cutout of a lateral surface of a cylinder having an axis of symmetry parallel to a longitudinal axis of the segment.

9. The segment according to claim 7, wherein at least one of the first flat structure and the second flat structure has a shape of a cutout of a lateral surface of a cone having an axis of symmetry parallel to a longitudinal axis of the segment.

* * * * *